United States Patent
Vaitekunas

[19]

[11] Patent Number: 5,980,544
[45] Date of Patent: Nov. 9, 1999

[54] BALLISTIC SPECIMEN BAG FOR USE WITH ULTRASONIC DEVICES

[75] Inventor: Jeffrey J. Vaitekunas, West Chester, Ohio

[73] Assignee: Ethicon Endo-Surgery, Inc., Cincinnati, Ohio

[21] Appl. No.: 09/080,737

[22] Filed: May 18, 1998

[51] Int. Cl.⁶ .................................................. F61B 17/32
[52] U.S. Cl. ................................ 606/169; 600/37; 604/33
[58] Field of Search ............................. 606/169; 600/37; 604/33, 22, 24, 164, 165, 166; 383/109

[56] References Cited

U.S. PATENT DOCUMENTS

| | | | |
|---|---|---|---|
| 4,531,934 | 7/1985 | Kossovky et al. | 604/22 |
| 5,037,379 | 8/1991 | Clayman et al. | 600/37 |
| 5,094,794 | 3/1992 | Croman et al. | 264/174 |
| 5,143,082 | 9/1992 | Kindberg et al. | 128/749 |
| 5,215,521 | 6/1993 | Cochran et al. | 604/22 |
| 5,224,930 | 7/1993 | Spaeth et al. | 604/33 |
| 5,327,896 | 7/1994 | Schmieding | 128/753 |
| 5,395,671 | 3/1995 | Coppage, Jr. et al. | 428/102 |
| 5,403,276 | 4/1995 | Schechter et al. | 604/22 |
| 5,419,761 | 5/1995 | Nanayanan et al. | 604/22 |
| 5,443,472 | 8/1995 | Li | 606/114 |
| 5,514,086 | 5/1996 | Parisi et al. | 604/22 |
| 5,520,634 | 5/1996 | Fox et al. | 604/22 |
| 5,709,671 | 1/1998 | Stephens et al. | 604/455 |
| 5,769,794 | 6/1998 | Conlan et al. | 600/37 |

OTHER PUBLICATIONS

Physics of Ultrasonic Surgery Using Tissue Fragmentation, W.W. Cimino and L.J. Bond, 1995 IEEE Ultrasonics Symposium pp. 1597–1600.

Military Standard V50 Ballistic Test for Armor, MIL–STD–662E, dated Jan. 22, 1987.

Miltary Specification, Cloth, Ballistic, Nylon, MIL–C–12369 (GL) Jun. 28, 1994, Superceding MIL–C–12369E (GL) Jul. 25, 1977.

Military Specification, Cloth, Ballistic, Nylon, MIL–C–12369f (GL), dated Jun. 28, 1974 and Amendment–1 dated Aug. 17, 1977.

*Primary Examiner*—Michael Buiz
*Assistant Examiner*—Lien Ngo
*Attorney, Agent, or Firm*—Bernard Shay

[57] ABSTRACT

With the advent of laparoscopic and endoscopic surgery, the patient is benefiting from shorter hospitalization, less pain, and generally better outcomes. However, the minimization of the size of incision a surgeon uses in these procedures has created some unique challenges. Large tissue masses, such as fibroid tissue masses, are traditionally excised during the surgical procedure and removed intact from the patient through the surgical incision. One common procedure for reducing the size of large tissue masses is generally referred to as morcellation. In the present invention, a ballistic specimen bag is described for use with ultrasonic surgical instruments. The ballistic specimen bag comprises a proximal end, a distal end, and an opening at the proximal end. A sheet surrounds the opening, extending from the proximal end and enclosing the distal end. The sheet comprises cloth woven from a material having ballistic characteristics. The ballistic specimen bag may be manufactured from a sheet having a $V_{50}$ attribute greater than or equal to approximately 1225 feet per second.

18 Claims, 10 Drawing Sheets

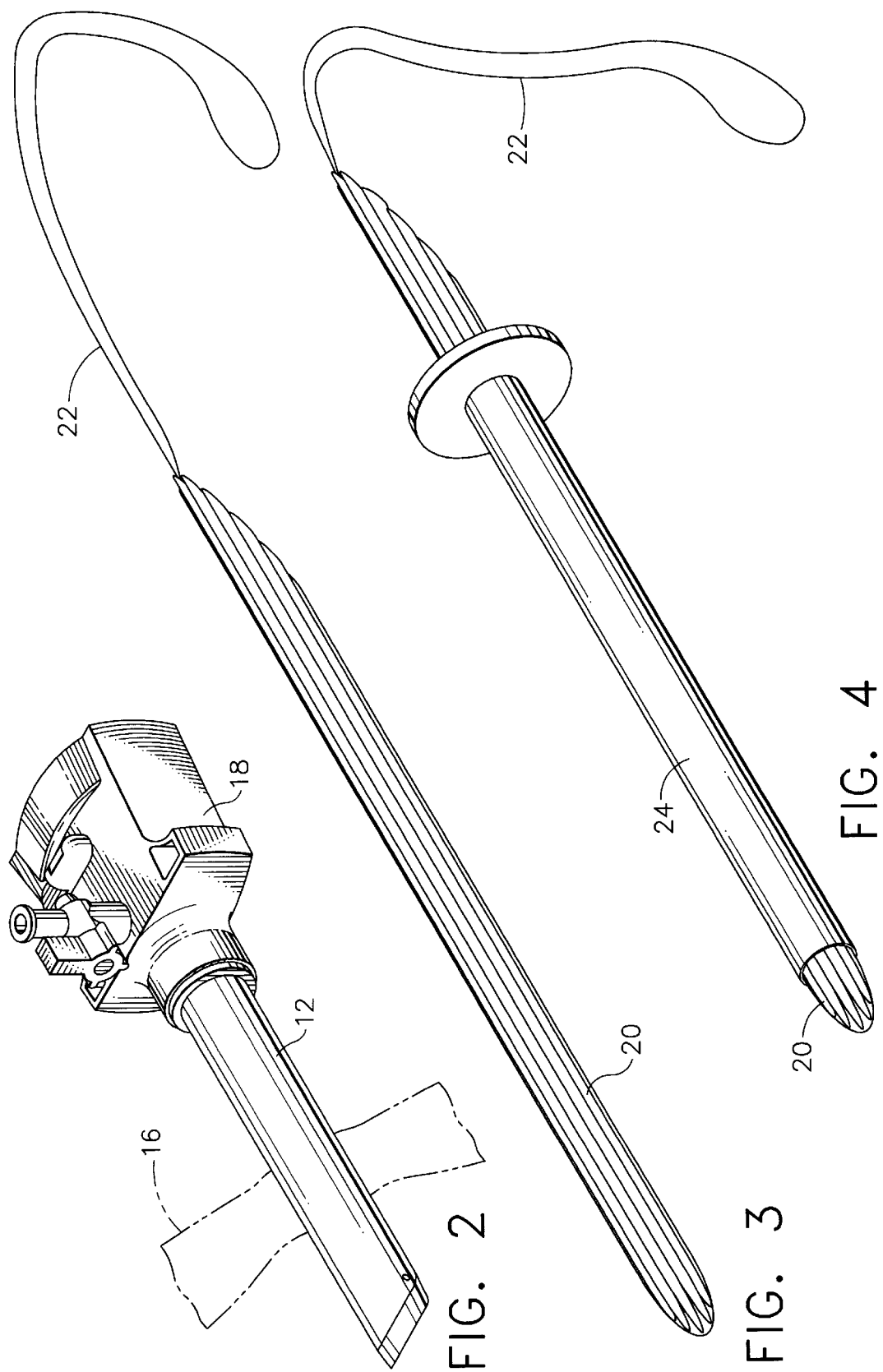

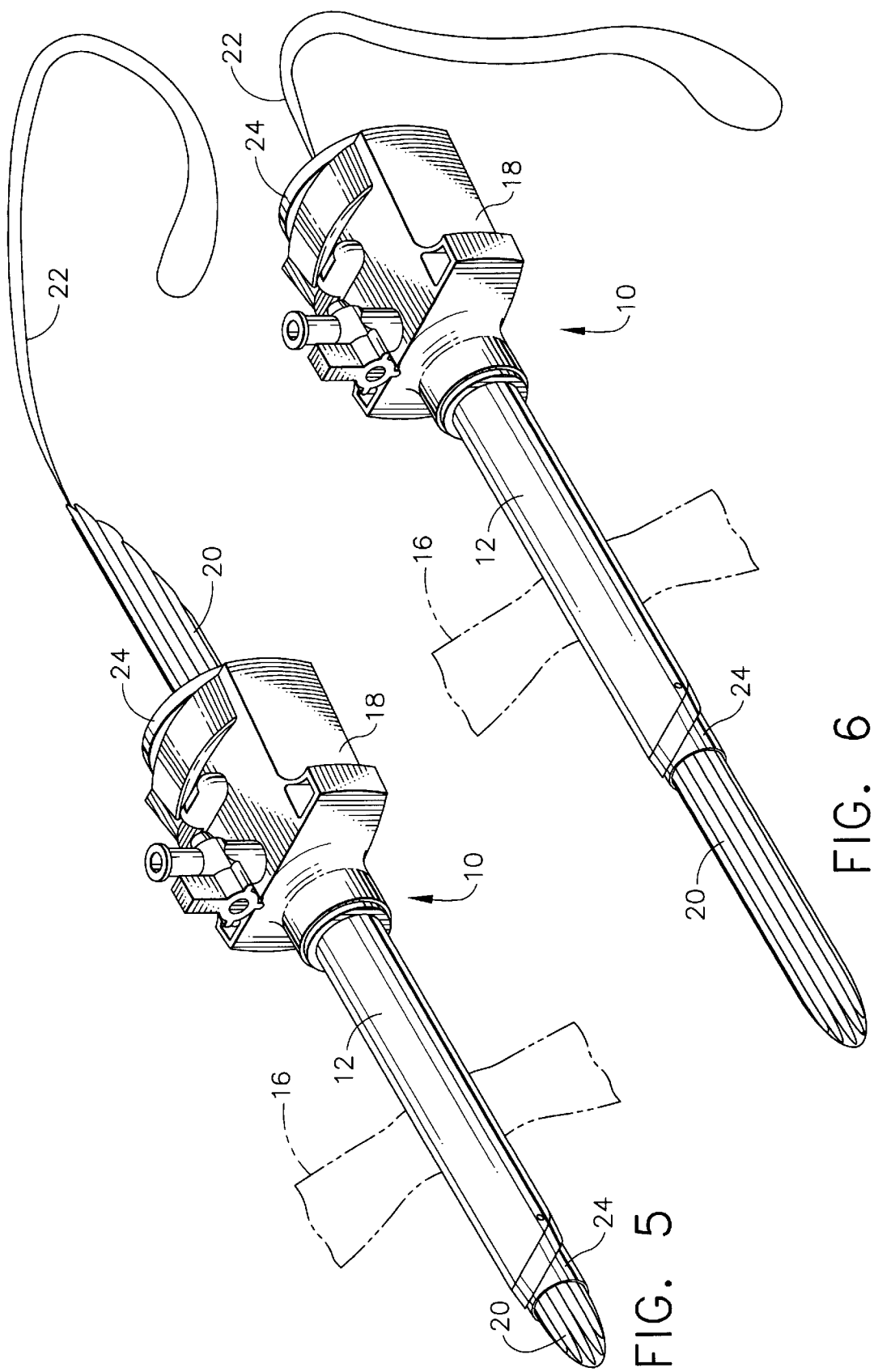

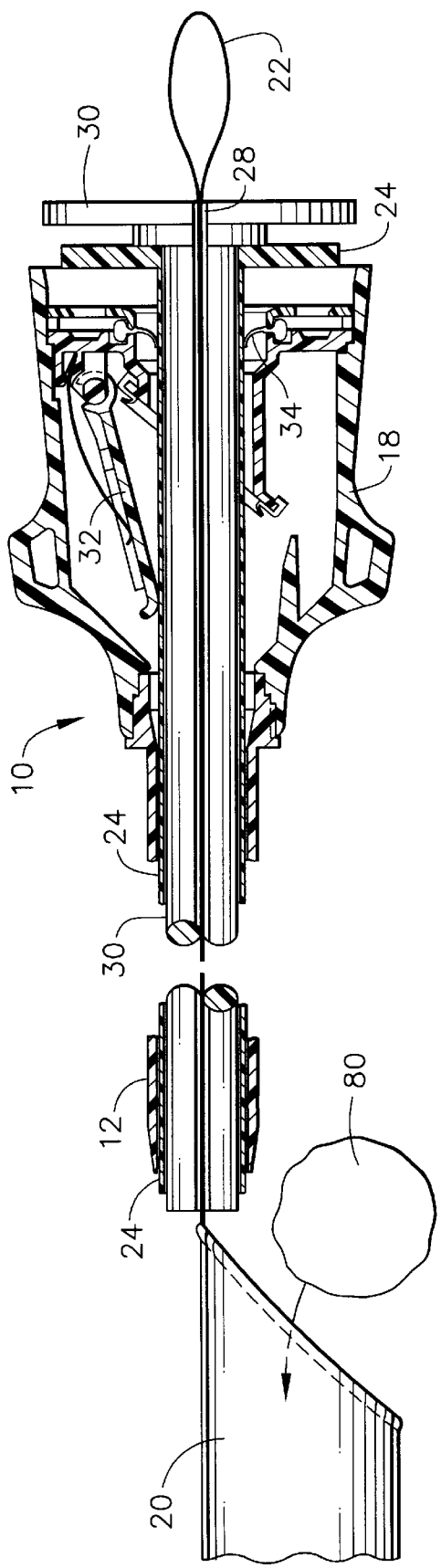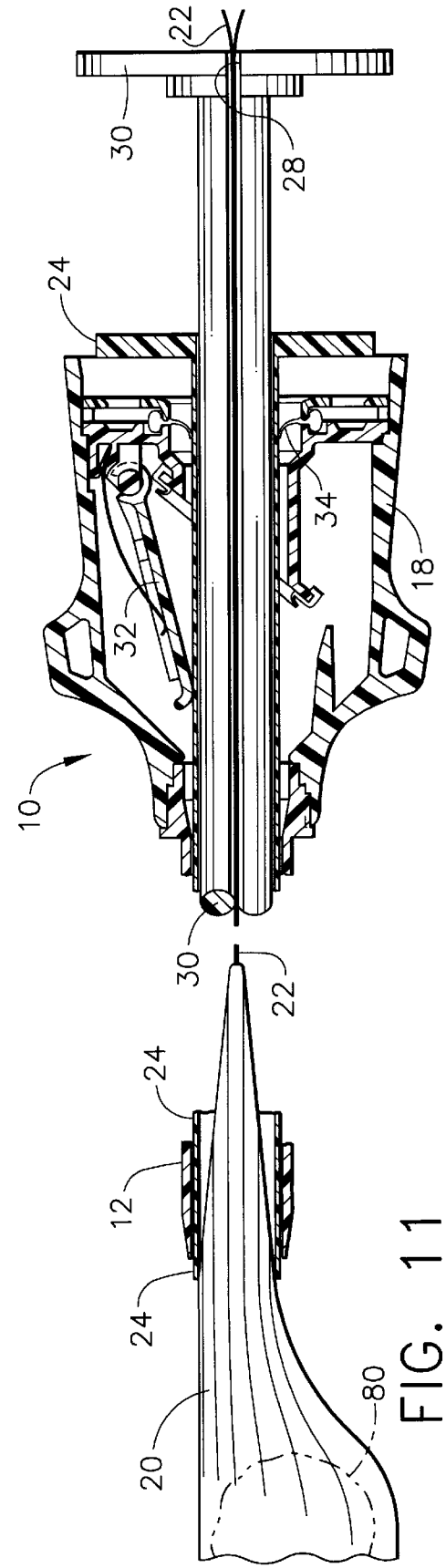
FIG. 10
FIG. 11

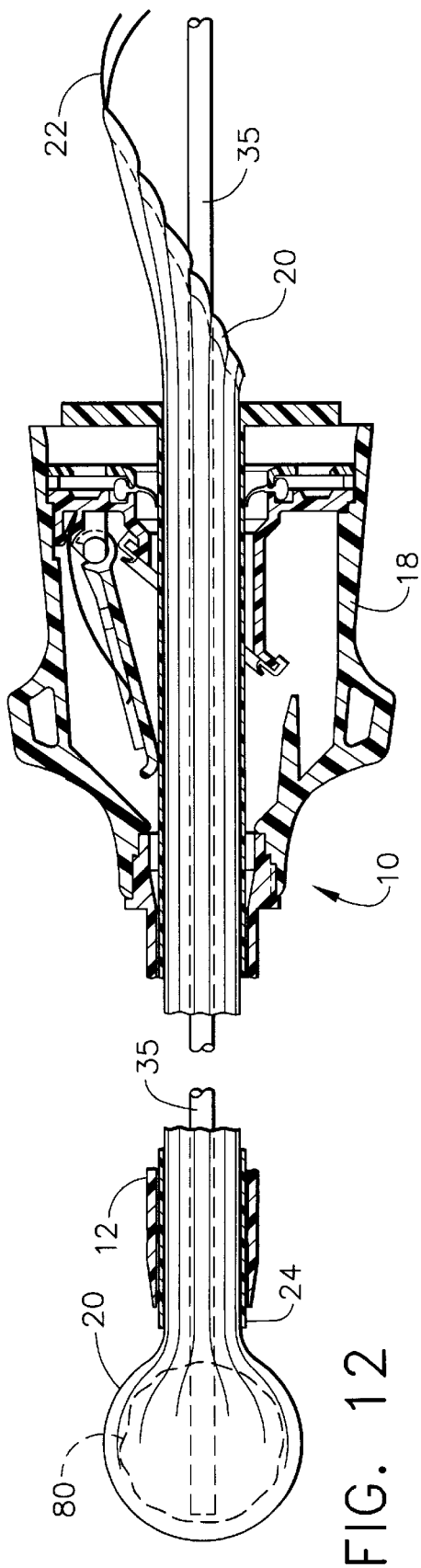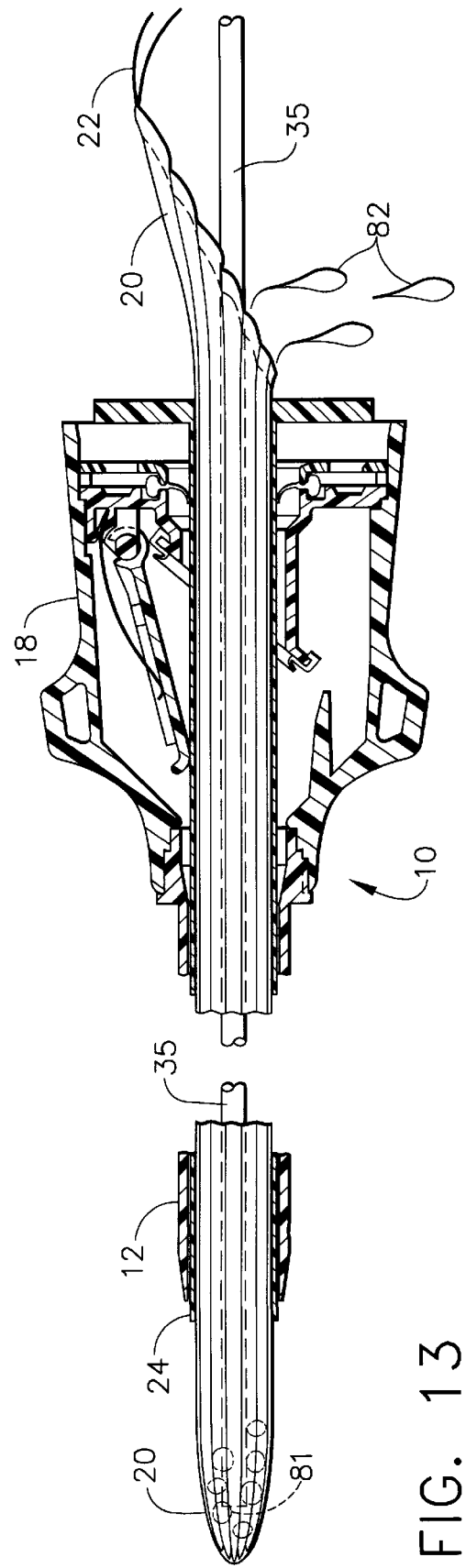

BALLISTIC SPECIMEN BAG FOR USE WITH ULTRASONIC DEVICES

This application is related to the following copending U.S. patent applications: application Ser. No. 08/811,704 filed Mar. 5, 1997; and application Ser. No. 09/080,870 filed May 18, 1998 [Attorney Docket No. END-540]; which are hereby incorporated herein by reference.

FIELD OF THE INVENTION

The present invention relates, in general, to specimen bags for use in morcellation during surgery and, more particularly, to a specimen bag constructed of a ballistic material which is particularly adapted for use with an ultrasonic morcellation instrument.

BACKGROUND OF THE INVENTION

With the advent of laparoscopic and endoscopic surgery, surgical patients are benefiting from shorter hospitalization, less pain, and generally better outcomes. However, the minimization of the size of incision a surgeon uses in these procedures has created some unique challenges.

Large tissue masses, such as fibroid tissue masses, are traditionally excised during the surgical procedure and removed intact from the patient through the surgical incision. These masses can easily be 3 centimeters in diameter or larger. In minimally invasive surgery, the operation is typically conducted using incisions of less than 1 centimeter, and often 5 millimeters or less. Thus, the trend toward the use of minimally invasive surgery has created a need to reduce large tissue masses to a size small enough to fit through an opening which may be 1 centimeter or smaller in size. One common procedure for reducing the size of large tissue masses is generally referred to as morcellation.

A surgeon performing a minimally invasive surgical procedure, such as, for example, a laparoscopic cholecystectomy, will often make three small incisions in the patients abdominal wall. A medial incision may be used for insertion of a video system, and two lateral incisions may be used for surgical instrumentation. If the incisions are small (e.g. 5 mm trocar ports), and the gallbladder contains stones larger than 5 mm in diameter, the stones may be morcellated and removed through a trocar inserted in one of the lateral incisions. Morcellation is facilitated by placing a specimen bag into the abdominal cavity and opening the specimen bag to facilitate access to the interior of the specimen bag. Specimen bags which are used for morcellation may also be referred to as containment bags or morcellation bags. Drawstrings for the specimen bag opening may be either inside the abdominal cavity, or alternatively, a portion of the strings may extend through the trocar outside the patient's abdominal wall.

In a laparoscopic cholecystectomy the entire gallbladder, containing stones and bile, is excised and inserted into the specimen bag. The bag opening may now be closed by pulling the drawstrings. The surgeon may continue to pull the drawstrings out of the trocar port, bringing a portion of the specimen bag to the outside of the patients abdominal wall, and leaving a portion of the specimen bag with the gallbladder and contents inside the patients abdominal cavity. The tissue in the bag may then be morcellated to facilitate removal of the bag and its contents through the trocar.

Specially designed medical instruments, which are generally referred to as morcellators, have been developed to reduce the volume of excised tissue before it is removed from the patient. See, for example, the instruments described in U.S. Pat. Nos.: 5,037,379; 5,40:3,276; 5,520,634; 5,327,896 and 5,443,472. As those references illustrate, excised tissue is morcellated (i.e. debulked), collected and removed from the patient's body through, for example, a surgical trocar or directly through one of the surgical incisions.

Mechanical morcellators cut tissue using, for example, sharp end-effectors such as rotating blades. Electrosurgical and ultrasonic morcellators use energy to morcellate tissue. For example, a system for fragmenting tissue utilizing an ultrasonic surgical instrument is described in "Physics of Ultrasonic Surgery Using Tissue Fragmentation", 1995 IEEE Ultrasonics Symposium Proceedings, pages 1597–1600.

In order to prevent morcellated tissue from spreading to other parts of the body during and after the morcellation procedure, the excised tissue is, in most cases, placed in a specimen bag prior to being morcellated. However some morcellators are used without specimen bags. Specimen bags are, therefore, designed to hold excised tissue without spilling tissue, or tissue components, into the abdominal cavity during morcellation. It will be apparent that specimen bags used with morcellators must be strong enough to prevent tears or cuts which might spill the contents of the specimen bag.

Ultrasonic morcellation instruments may be particularly advantageous for use in certain surgical procedures and for debulking certain types of tissue. When using any morcellator it is important to ensure that the end effector of the morcellator does not penetrate the specimen bag. This concern is particularly applicable to ultrasonic morcellation instruments where the tip of the debulking end effector may have an excursion of between 50 and 300 micrometers, which would correspond to tip peak velocities ranging from 8.7 meters per second to 52.3 meters per second at 55,500 Hertz.

Thus, in an ultrasonic morcellator, there is potential for the tip of the end effector to penetrate the wall of conventional specimen bags. An ultrasonic surgical instrument tip vibrating at approximately 55,500 cycles per second may create a significant potential for fatigue and abrasion of the interior wall of conventional specimen bags, weakening the bag and making it susceptible to tearing as it is pulled out through the trocar.

A blunt or rounded ultrasonic morcellator tip reduces the possibility of unintended cutting or tearing of the specimen bag while the ultrasonic energy morcellates the tissue. U.S. Pat. No. 5,449,370, hereby incorporated herein by reference, describes a blunt tipped ultrasonic surgical instrument capable of morcellating tissue contained within a specimen bag (FIGS. 1–3, and text from Col. 3, line 44 to Col. 6, line 8 of U.S. Pat. No. 5,449,370). However, current specimen bags may be weakened or punctured when using an ultrasonic surgical instrument such as the one described in U.S. Pat. No. 5,449,370.

It would, therefore, be advantageous to design a specimen bag which is particularly adapted for use with an ultrasonic morcellation instrument. More particularly, it would be advantageous to design a specimen bag with unique properties which make the bag substantially impervious to the end effector of an ultrasonic morcellation instrument. Further, it would be advantageous to design a morcellator specimen bag which is strong enough to withstand the impact and abrasion of an ultrasonic end-effector while remaining substantially impervious to fluids.

SUMMARY OF THE INVENTION

A ballistic specimen bag is described for use with ultrasonic surgical instruments. The ballistic specimen bag comprises a proximal end, a distal end, and an opening at the proximal end. A sheet surrounds the opening, extending from the proximal end and enclosing the distal end. The sheet comprises cloth woven from a material having ballistic characteristics.

In one embodiment of the present invention the ballistic specimen bag may be manufactured from ballistic nylon, and may be impregnated with a sealant such as silicone. In another embodiment of the present invention the ballistic specimen bag may be manufactured from a ballistic material such as KEVLAR or SPECTRA. A ballistic specimen bag in accordance with the present invention may also be coated or impregnated with a sealant. In a further embodiment, the ballistic specimen bag may be manufactured from a sheet of ballistic material having a $V_{50}$ attribute greater than or equal to approximately 1225 feet per second.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 2 is a isometric view of the cannula and housing of the trocar illustrated in FIG. 1 after entry into the body cavity.

FIG. 3 is a isometric view of a preferred embodiment of a ballistic specimen bag according to the present invention wherein the ballistic specimen bag is constructed of fluted ballistic material.

FIG. 4 is a isometric view of a ballistic specimen bag according to the present invention in assembly with an insertion tube.

FIG. 5 is a isometric view of the insertion tube and ballistic specimen bag assembly illustrated in FIG. 4 after it has been inserted into the cannula illustrated in FIG. 2.

FIG. 6 is a isometric view of the ballistic specimen bag after it has been moved distally to extend out the end of the cannula and insertion tube combination.

FIG. 10 is a view partially in section illustrating the insertion of a tissue mass into a ballistic specimen bag according to the present invention while the insertion tube and pusher rod maintain cavity pressure.

FIG. 11 is a view partially in section illustrating the initial recovery of the proximal end of the ballistic specimen bag.

FIG. 12 is a view partially in section illustrating the distal end of an ultrasonic surgical instrument inserted into the ballistic specimen bag in preparation for morcellating the tissue mass.

FIG. 13 is a view partially in section illustrating that the ultrasonic surgical instrument has morcellated and partially liquefied the tissue mass sufficiently to remove the bag and ultrasonic rod through the cannula.

DETAILED DESCRIPTION OF THE INVENTION

Figure 1:
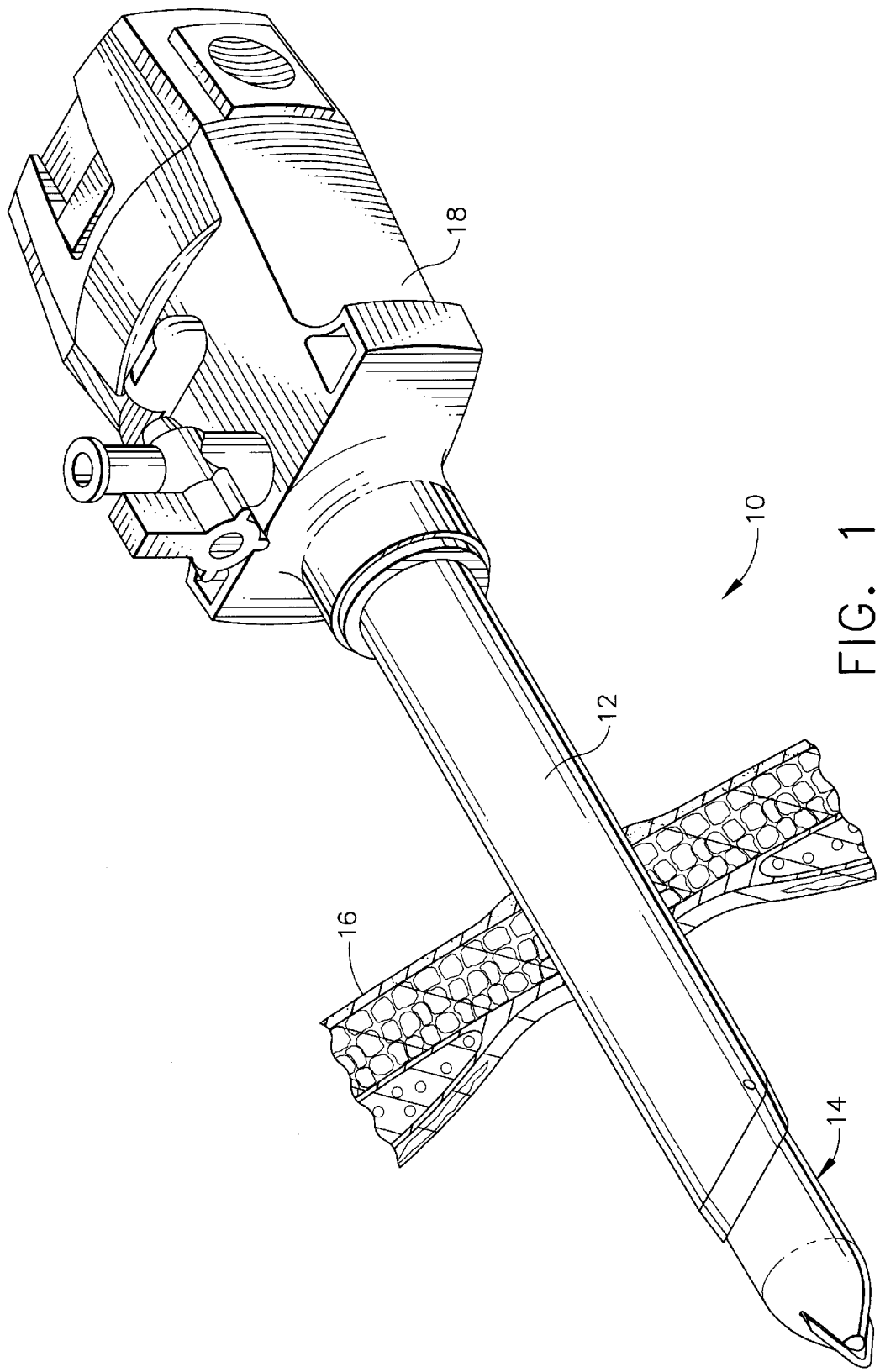
FIG. 1 is a isometric view of a trocar which may be used with a ballistic specimen bag according to the present invention.

FIG. 1 is a isometric view of a trocar 10 comprising cannula 12, cannula housing 18, and obturator 14. In trocar 10, obturator 14 is used for piercing abdominal wall 16 of a patient. After the abdominal wall 16 is pierced, cannula 12 is positioned in the abdominal wall 16 to provide a port of entry through the abdominal wall 16 as illustrated in FIG. 2. FIG. 2 is a isometric view of cannula 12, including cannula housing 18, after cannula 12 has been inserted through abdominal wall 16. A suitable trocar for use with the present invention is illustrated and described in U.S. Pat. No. 5,709,671 which was previously incorporated herein by reference.

FIG. 3 is a isometric view of a preferred embodiment of a ballistic specimen bag 20 according to the present invention wherein the ballistic specimen bag 20 is constructed of ballistic material. In the embodiment illustrated in FIG. 3, ballistic specimen bag 20 includes drawstring 22. FIG. 4 is a isometric view of ballistic specimen bag 20 in insertion tube 24. Insertion tube 24 may also be referred to as a shipping tube.

FIGS. 5 through 15 illustrate medical methods for reducing and removing excised tissue mass 80 (FIG. 10) utilizing a ballistic specimen bag 20 according to the present invention. FIG. 5 is a isometric view illustrating insertion tube 24 and ballistic specimen bag 20 after they have been inserted into cannula 12 of trocar 10, with cannula 12 positioned through abdominal wall 16.

FIG. 6 is a isometric view illustrating trocar 10, ballistic specimen bag 20 and insertion tube 24. In FIG. 6, ballistic specimen bag 20 has been moved distally to extend from the distal end of cannula 12. Ballistic specimen bag 20 may be moved through cannula 12 by, for example, manual manipulation or by using a pusher rod 30 (shown in FIG. 7) or other instrument.

Figure 7:
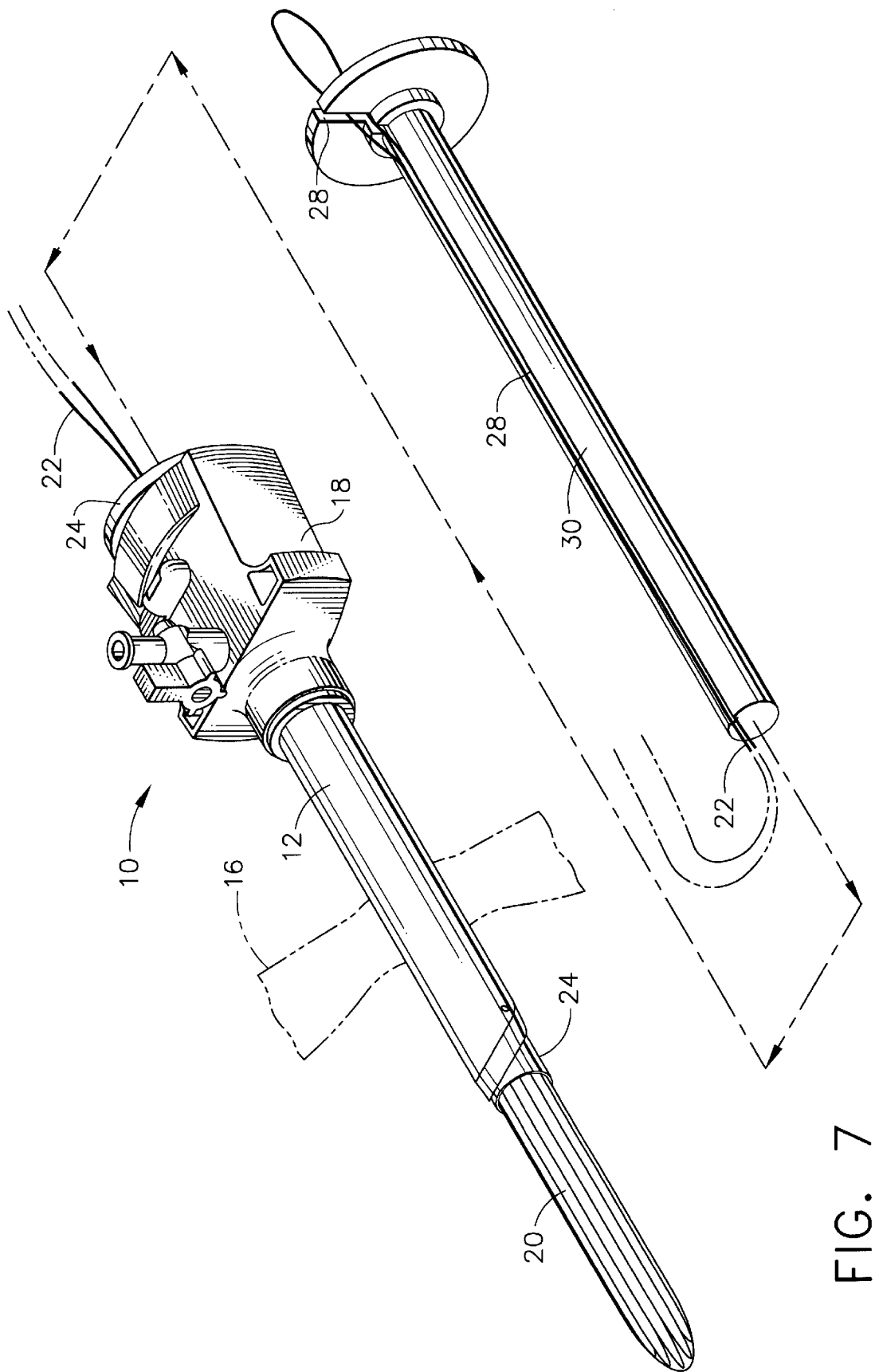
FIG. 7 is an exploded isometric view of the ballistic specimen bag, tube and cannula combination in conjunction with a pusher rod.

FIG. 7 is an exploded isometric view illustrating how ballistic specimen bag 20 and insertion tube 24 are positioned in cannula 12 of trocar 10. Pusher rod 30 may be used to push ballistic specimen bag 20 through insertion tube 24, and into the abdominal cavity. Drawstring 22 lies within drawstring groove 28 of pusher rod 30 during insertion of ballistic specimen bag 20 into the abdominal cavity. Drawstring groove 28 provides a pathway for drawstring 22 to reduce possible binding between insertion tube 24 and pusher rod 30 during insertion of pusher rod 30 into insertion tube 24.

Figure 8:
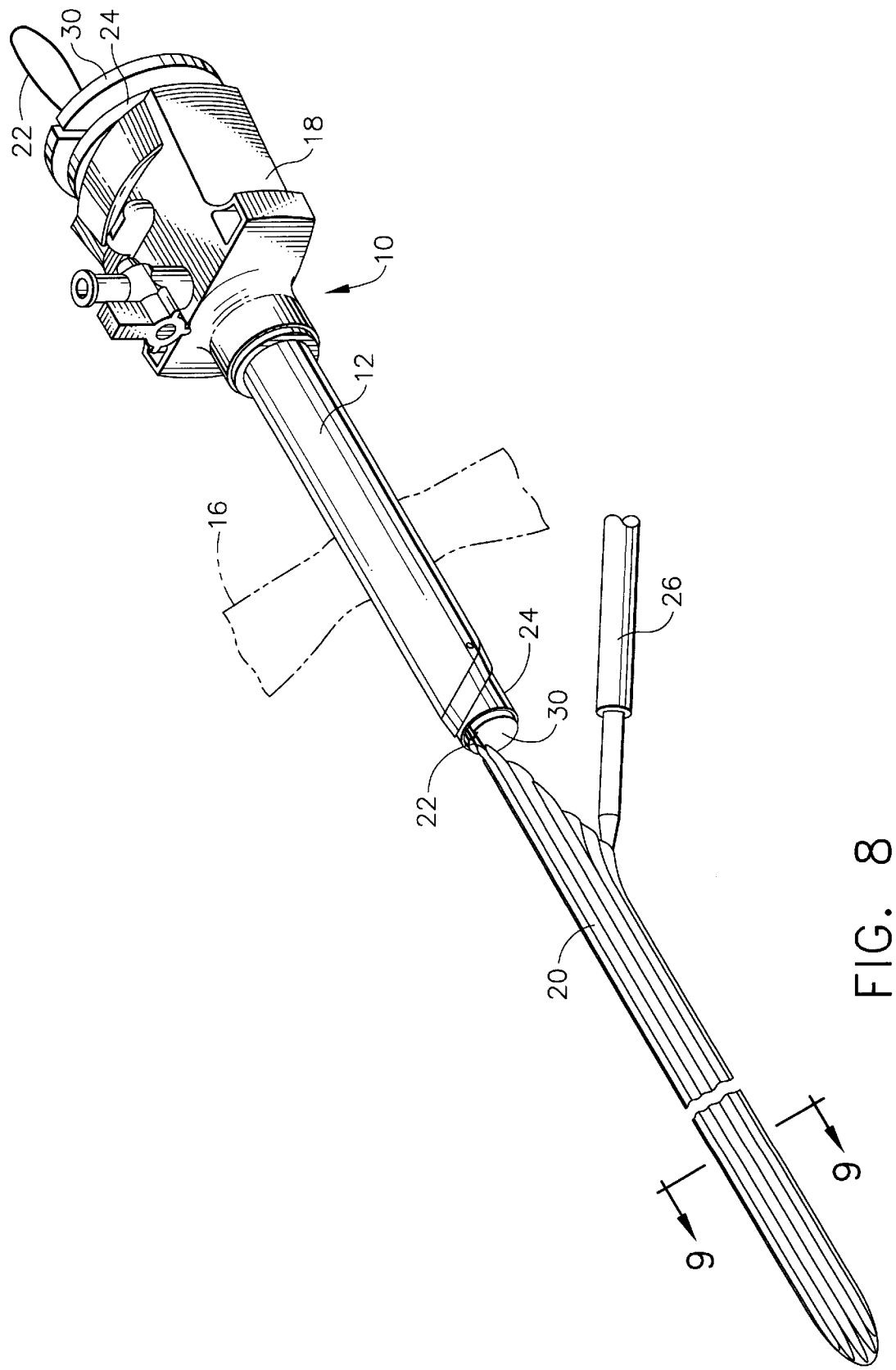
FIG. 8 is a isometric view of the ballistic specimen bag after it has been fully inserted into the body cavity, wherein a surgical dissector instrument is used to open the ballistic specimen bag.

FIG. 8 is a isometric view of the ballistic specimen bag 20 after it has been fully inserted into the body cavity by the pusher rod 30. Note that a surgical dissector 26 is about to open the ballistic specimen bag 20. Pusher rod 30 is inserted through insertion tube 24. Drawstring 22 lies within drawstring groove 28 (FIG. 7), between pusher rod 30 and insertion tube 24. Drawstring 22 extends through cannula 12 and abdominal wall 16, out of trocar 10, to the outside of the abdominal cavity.

Figure 9:
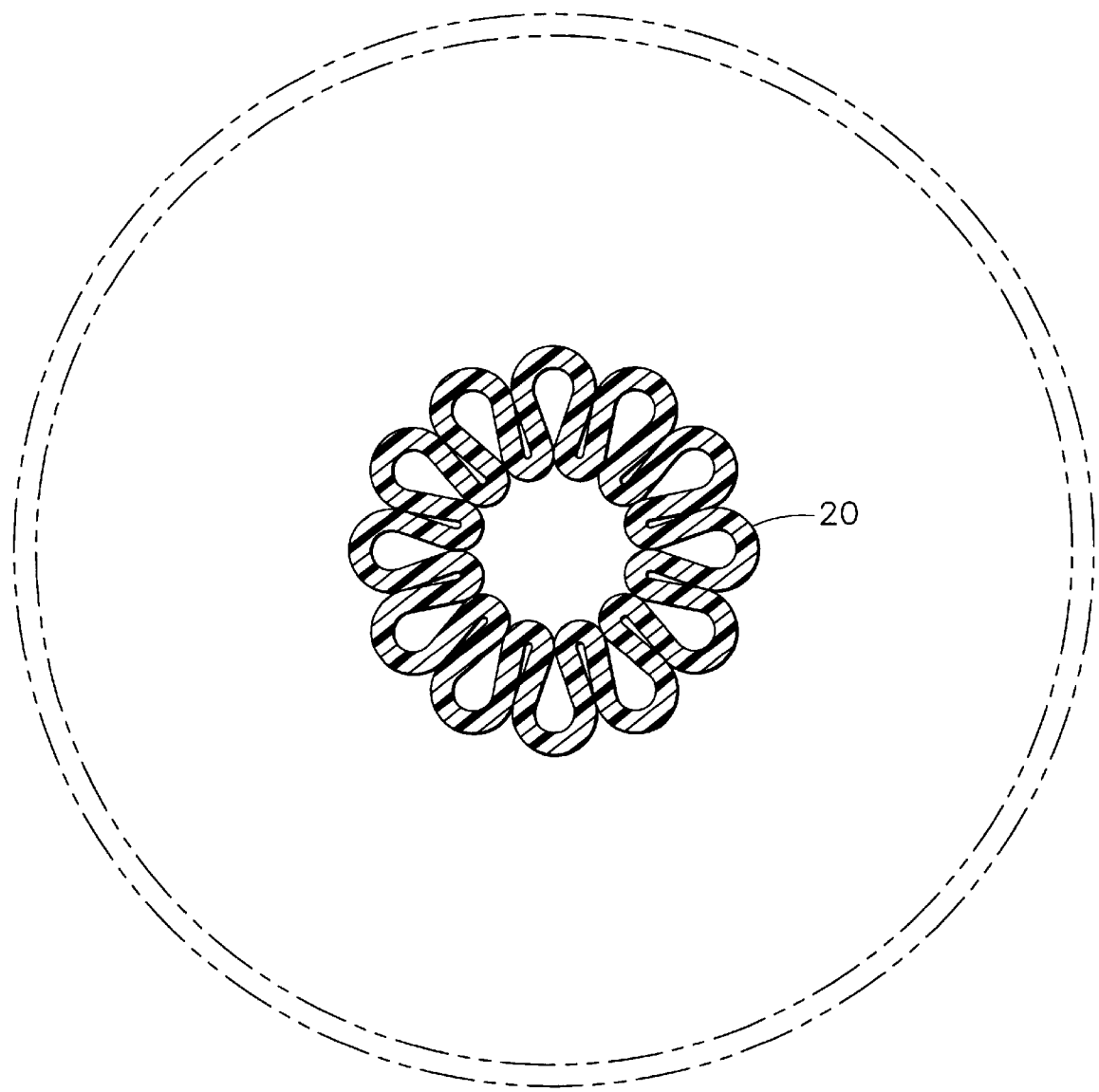
FIG. 9 is an enlarged cross section view taken along line 9—9 of FIG. 8 with an expanded ballistic specimen bag according to the present invention shown in phantom.

FIG. 9 is an enlarged cross section view taken along line 9—9 of FIG. 8. The circles shown in phantom illustrate the ballistic specimen bag 20 in its open condition. In solid lines, ballistic specimen bag 20 is shown folded into a fluted pattern preferable for positioning within insertion tube 24 (shown in FIG. 4). The fluted pattern allows a large ballistic specimen bag 20 to be inserted through a small cannula such as cannula 12 (FIG. 8).

FIG. 10 is a view partially in section illustrating the insertion of a tissue mass 80 into the ballistic specimen bag 20. Pusher rod 30 fills insertion tube 24. Insertion tube 24 is in contact with seal 34 to maintain pressure within the abdominal cavity. Insertion tube 24 holds flapper valve 32 open, providing a passage through trocar 10 for pusher rod 30 and ballistic specimen bag 20.

FIG. 11 is a view partially in section illustrating the initial recovery of the ballistic specimen bag 20. As the ballistic specimen bag 20 fills insertion tube 24, pusher rod 30 will come out of trocar 10 as the surgeon pulls on the drawstring 22. Pulling drawstring 22 will also close ballistic specimen bag 20, maintaining tissue mass 80 within ballistic specimen bag 20.

FIG. 12 is a view partially in section illustrating an ultrasonic surgical instrument 35 inserted into the ballistic specimen bag 20 in preparation for morcellating the tissue mass 80. Tissue mass 80 is held against the distal extremity of insertion tube 24 and cannula 12 by ballistic specimen bag 20. Ultrasonic surgical instrument 35 is inserted through trocar 10, inside of ballistic specimen bag 20, and energized, morcellating tissue mass 80 into fragments 81 and liquid 82 as shown in FIG. 13.

FIG. 13 is a view partially in section illustrating that the ultrasonic surgical instrument 35 has fragmented and partially liquefied the tissue mass 80 sufficiently to remove the ballistic specimen bag 20 and ultrasonic surgical instrument 35 through the cannula 12. Cannula 12 stays in place and continues to hold abdominal cavity pressure. Any tissue mass material draining from ballistic specimen bag 20 does so on the outside of abdominal wall 16.

Figure 14:
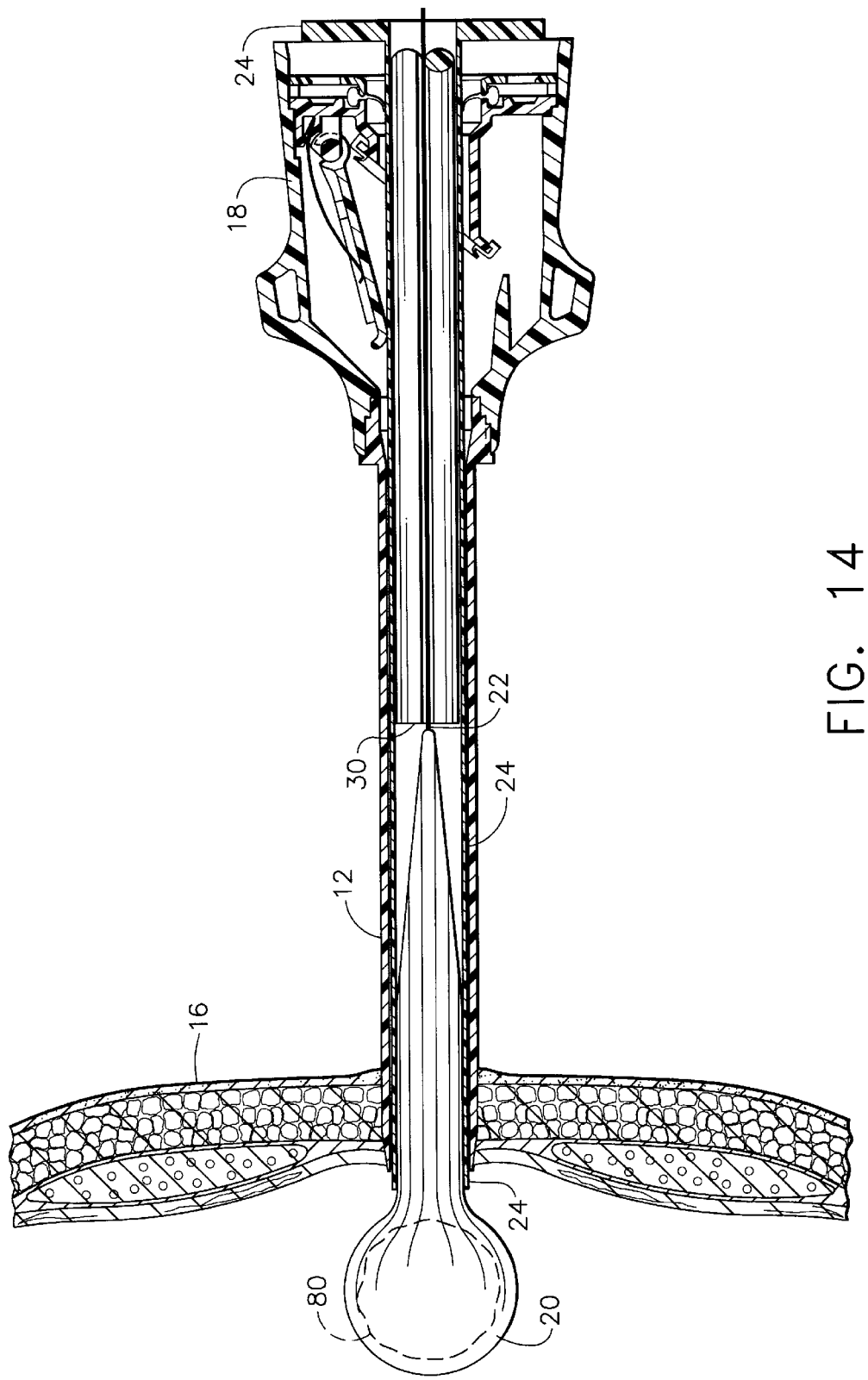
FIG. 14 is a view partially in section illustrating an alternative morcellation procedure wherein the trocar is removed before the tissue mass is morcellated.
Figure 15:
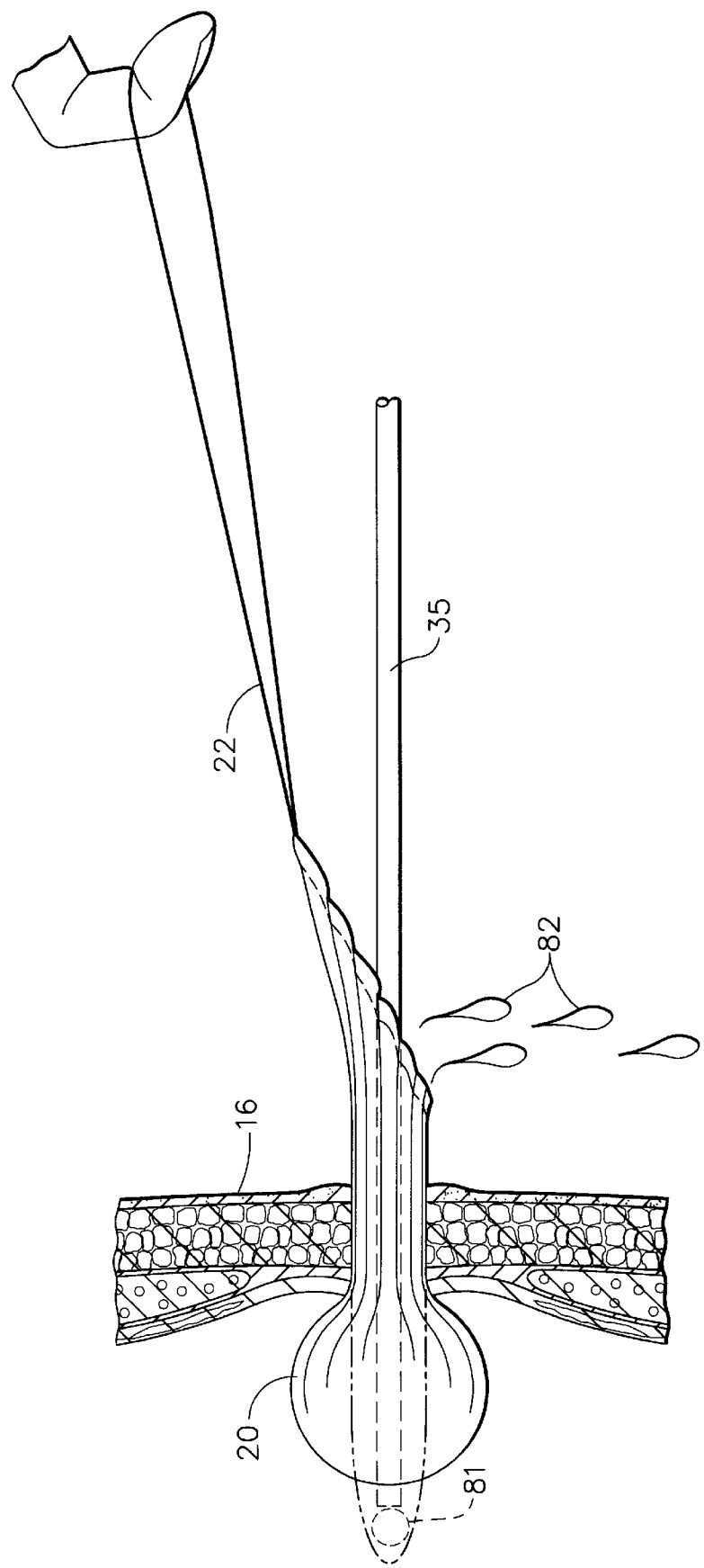
FIG. 15 is a view partially in section illustrating the ballistic specimen bag tensioned against the inside of the abdominal wall during morcellation of the tissue mass by an ultrasonic surgical instrument.

FIG. 14 is a view partially in section illustrating an alternate procedure using ballistic specimen bag 20 for the morcellation of tissue mass 80. In the procedure illustrated in FIG. 14, cannula 12, insertion tube 24, and pusher rod 30 are being removed from the abdominal wall 16 before morcellation of tissue mass 80. FIG. 15 is a view partially in section illustrating the ballistic specimen bag 20 tensioned against the inside of abdominal wall 16 while an ultrasonic surgical instrument 35 reduces the tissue mass 80 to fragments 81 and liquid 82 until the bag collapses enough to exit the incision.

Ultrasonic surgical instrument 35 is inserted through abdominal wall 16 into ballistic specimen bag 20 which contains tissue mass 80. Ultrasonic surgical instrument 35 vibrates longitudinally at an ultrasonic frequency, such as 55.5 kHz. The excursion of ultrasonic surgical instrument 35 impacts tissue mass 80, causing it to fragment or emulsify, and reducing its bulk from a single large mass to several smaller masses, or a slurry.

Ballistic specimen bag 20 contains at least one layer of a ballistic material, and may also include leak resistive layer such as, for example, silicone rubber. The leak proofing layer may be applied to the outside of the ballistic layer by, for example, impregnation, coating, or layering. This can be accomplished through known processes such as spraying or dipping the ballistic specimen bag with a material such as silicone rubber.

One parameter, the ballistic impact resistance of a material, can be utilized to quantify the ability of the ballistic specimen bag material to withstand morcellation of tissue with an ultrasonic surgical instrument. For the purpose of the present invention, ballistic materials will be defined as materials which are capable of being formed into ballistic specimen bags and which meet the requirements of military standard MIL-STD-662E. As set forth in that standard, the parameter '$V_{50}$' (Ballistic Test for Armor) defines a velocity attribute which can be attributed to certain materials, specifically woven cloths.

The $V_{50}$ ballistic limit, in general, is the velocity at which there is a 50 percent probability of penetration of a material by a projectile with specific physical characteristics. Determining if a woven material exceeds a $V_{50}$ value of 1225 feet per second is accomplished using the following procedure:

1. Prepare four test panels of material for testing, with each panel consisting of 12 layers of unbonded material and each layer being approximately 15 inches by 15 inches in size. Precondition test panels in the test area for at least 48 hours prior to conducting the ballistic test with air (at 23+/−2 degrees Centigrade and 50+/−5% relative humidity) freely circulating on all sides of the panels.
2. Place a witness plate of 0.5 mm thick 2024-T3 Aluminum 6+/−0.5 inches behind each panel, parallel to the panels. The witness plate must be of sufficient size to be impacted by all fragments resulting from projectile penetration through the panels.
3. Subject each panel to 10 fair impacts of 0.22 caliber blunt tipped, copper plated lead, 40 grain weight projectiles traveling at 1225+/−90 feet per second velocity. (An impact shall be considered fair when an unyawed projectile strikes an unsupported area of the panel at a distance of at least two projectile diameters from any previous impact or disturbed area of the panel.)
4. Inspect each witness plate subsequent to 10 fair impacts, and sum the number of projectiles which have penetrated the panels. (Out of a sum total possible 40 penetrations). If the sum of penetrations for a given material is 20 or fewer, the material shall be deemed to be a ballistic material.

Ballistic Nylon, having a $V_{50}$ value for 12 layers of unbonded cloth greater or equal to 1225 feet per second, is one material which can be used in containment bags in accordance with the present invention. Other materials having ballistic characteristics such as, for example, KEVLAR and SPECTRA, trademark names of E. I. Du Pont de Nemours and Company for very high molecular weight polymer materials, described in U.S. Pat. Nos. 5,395,671; and 5,094,794, may also be used.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An ultrasonic surgical system for tissue morcellation comprising:
   an ultrasonic surgical instrument comprising:
   an ultrasonic transducer;
   a waveguide coupled to said transducer;
   an end effector coupled to said waveguide;

a ballistic specimen bag comprising:
  a proximal end;
  a distal end;
  an opening at said proximal end; and
  a sheet surrounding said opening, extending from said proximal end and enclosing said distal end, wherein said sheet comprises cloth woven from a material having ballistic characteristics:
wherein said ultrasonic surgical instrument is insertable into said ballistic specimen bag.

2. An ultrasonic surgical system according to claim 1, wherein said sheet comprises ballistic nylon.

3. An ultrasonic surgical system according to claim 2, wherein said sheet includes a sealant.

4. An ultrasonic surgical system according to claim 3 wherein said sealant comprises silicone.

5. An ultrasonic surgical system according to claim 1 wherein said sheet comprises KEVLAR.

6. An ultrasonic surgical system according to claim 5, wherein said sheet is impregnated with a sealant.

7. An ultrasonic surgical system according to claim 6 wherein said sealant comprises silicone.

8. An ultrasonic surgical system according to claim 1, wherein said sheet has a $V_{50}$ attribute greater than or equal to approximately 1225 feet per second.

9. An ultrasonic surgical system according to claim 8, wherein said sheet is impregnated with a sealant.

10. An ultrasonic surgical system according to claim 9 wherein said sealant comprises silicone.

11. An ultrasonic surgical system according to claim 8, wherein said sheet includes a sealant.

12. An ultrasonic surgical system according to claim 11 wherein said sealant comprises silicone.

13. An ultrasonic surgical system according to claim 1 wherein said sheet comprises SPECTRA.

14. An ultrasonic surgical system according to claim 13, wherein said sheet includes a sealant.

15. An ultrasonic surgical system according to claim 14 wherein said sealant comprises silicone.

16. An ultrasonic surgical system ballistic specimen bag for use with ultrasonic surgical instruments comprising:
  an ultrasonic surgical instrument comprising:
    an ultrasonic transducer;
    a waveguide coupled to said transducer;
    an end effector coupled to said waveguide;
  a ballistic specimen bag comprising:
    a proximal end;
    a distal end;
    an opening at said proximal end;
    sheet surrounding said opening, extending from said proximal end and enclosing said distal end, wherein said sheet comprises cloth woven from a material having $V_{50}$ attribute greater than or equal to approximately 1225 feet per second; and
    drawstring encircling said opening of said proximal end of said ballistic specimen bag.

17. An ultrasonic surgical system according to claim 16, wherein said sheet includes a sealant.

18. An ultrasonic surgical system according to claim 17 wherein said sealant comprises silicone.

* * * * *